United States Patent
Widgerow et al.

[11] Patent Number: 6,159,494
[45] Date of Patent: Dec. 12, 2000

[54] **TREATMENT OF POST OPERATIVE SCARS WITH A TAPE CONTAINING A GEL FROM *BULBINE FRUTESCENS***

[76] Inventors: Alan D Widgerow, 19 Buffalo Road, Gallo Manor, Sandton, Gauteng; Laurence A Chait, 33 Junction Road, Bramley, Johannesburg, both of South Africa

[21] Appl. No.: 09/204,982

[22] Filed: Dec. 3, 1998

[30] Foreign Application Priority Data

Dec. 3, 1997 [ZA] South Africa .......................... 97/10846

[51] Int. Cl.⁷ ............................. A61F 13/00; A61K 9/70; A61L 15/00; A61L 15/16; A01N 65/00
[52] U.S. Cl. .......................... 424/443; 424/445; 424/447; 424/195.1
[58] Field of Search ................................. 424/195.1, 444, 424/443, 447, 445; 602/42, 48, 54, 58, 41, 304

[56] References Cited

U.S. PATENT DOCUMENTS 4,707,360 11/1987 Brasey ................................... 424/94.1
5,368,553 11/1994 Newman .................................. 602/58
5,883,998 11/1998 Biederman et al. ..................... 424/401

OTHER PUBLICATIONS van Wyk et al., Medicinal Plants of South Africa, Briza Publications, Pretoria, South Africa, pp. 64 and 65, 1997.

van Staden, F., Knipholine from *Bulbine latifolia* and *Bulbine frutescens*, Phytochemistry vol. 35 (3), pp. 685–686, Feb. 1994.

*Primary Examiner*—David M. Naff
*Assistant Examiner*—Mike Meller
*Attorney, Agent, or Firm*—Myers Bigel Sibley & Sajovec

[57] ABSTRACT

Postoperative scars are treated by a method of applying a microporous paper tape to the scar running along the length of the scar. A contact medium is applied to the exposed surface of the tape and penetrates to the skin. The contact medium comprises an expressed gel from the plant *Bulbine frutescens* and may contain asiaticoside and panthenol. These active ingredients are contained in a pharmaceutically acceptable cream. The contact material is applied each morning and evening. The tape is replaced when it falls away from the skin normally, e.g. every seven days and the treatment is then continued. Improved scar healing results from the use of this method.

7 Claims, No Drawings

TREATMENT OF POST OPERATIVE SCARS WITH A TAPE CONTAINING A GEL FROM *BULBINE FRUTESCENS*

FIELD OF THE INVENTION

This invention relates to methods of treatment of post-operative scars and materials for use in such methods.

DESCRIPTION OF THE RELATED ART

Notwithstanding considerable literature as exemplified by the articles mentioned in this specification and many attempts by practitioners, the prevention of exaggerated scarring has remained an unsolved problem. Many methods have been tried including the use of pressure dressings, splints, the application of silicone gel, steroid injections, and radiotherapy but all have had limited success and at times unwanted side effects.

Because an immature scar, if put on intermittent stretch remains immature and may become hypertrophic, it is known to treat the scar by applying a self-adhesive tape to the wound to provide a support therefor. With occlusive tape dressings however bacterial growth may take place beneath the tape so that the tape has to be replaced at regular intervals. As this takes place when the patient has been discharged from hospital it is up to the responsibility of the patient to ensure the replacement of the tape. Experience has shown that very soon the patient ceases to take the necessary care and stops the treatment with concomitant loss of benefits. We have used a self-adhesive microporous tape which does not allow for the bacterial growth and lasts for a lengthy period of about two weeks before having to be replaced. This has proved to be reasonably successful but required up to six months for maturity to take place.

Topical treatment with silicone gel or silicone sheet dressing has also proved to be an efficacious method of the treatment and prevention of hypertrophic scars and keloid. It is thought that the silicone gel provides hydration of the scars. Here too it is necessary for the dressing to be changed at least daily to prevent bacterial growth and as mentioned above patients in general appear to find this task onerous and often do not comply with the regimen proposed by the surgeon.

SUMMARY OF THE INVENTION

According to one aspect of the invention there is provided a method of treating post-operative scars comprising (a) applying to the scar a tape which supports the scar in such a way as to minimise tension on the scar tissue and which permits the passage therethrough of a contact medium applied to the exposed surface of the tape so that medium will reach and treat the scar, and (b) then applying to the exposed surface of tape a contact medium incorporating a hydrating agent which hydrates the scar and preferably providing enhanced wound healing. We have found that the provision of support and hydration and especially in addition with an enhanced wound healing constituent acts together to provide surprisingly improved scar management and maturation.

DETAILED DESCRIPTION OF THE INVENTION

The wound healing constituent preferably comprises the active ingredient from the plant *Centella asiatica* of which asiaticoside is the main constituent, which is itself known to promote balanced Type 1 and Type 3 collagen production and to reduce the relative amount of Type 3 collagen produced and which will cause the winding down of the inflammatory process. This inflammatory modulation property of asiaticoside is thought to stop the conversion of the mature fibrocytes to myofibroblasts, the cell type known to be associated with thickened keloid type scars.

The asiaticoside comprises two constituents that provide enhanced healing. These are (i) the glycosides and (ii) the triterpenic fraction (referred to herein as "TTF" which is the total aglycone fraction of all the glycosides in the plant). The latter has been found to be the more active and therefore the glycoside is used in far greater (normally ten times greater) concentrations. Conveniently the TTF, comprises from about 0.8 percent to 1.3 percent, preferably 1.0 percent of the contact medium. If the glycoside is used it may comprise between about 7.5 percent and 12.5 percent of the contact medium, preferably 10.0 percent. (All proportions given herein are mass to volume—i.e. gm/100 ml.)

Hydration is believed to reduce water vapour loss and to restore homeostasis to the scar. The constituent that is capable of hydrating the scar preferably embodies large molecules that will not be absorbed by the skin but remain on the skin surface. Such molecules together with the tape ensures hydration and semi-occlusion of the wound. A preferred constituent is the expressed gel from the plant *Bulbine frutescens* (the leaf sap of *Bulbine natalensis*) (Herein after also referred to as "FLB") This product is known for the treatment of wounds, burns, rashes, itches, ringworm, cracked lips and herpes. The healing effect is thought to be mainly due to glycoproteins in the gel such as aloctin A and aloctin B. The gel also enhances the hydrating effect of the included panthenol. Damaged skin can lose water more rapidly then healthy skin. Water is the only principal that will plasticise the layers of the skin. The mucopolysaccharides and glycoproteins contained in the expressed gel from the plant *Bulbine frutescens* which is a known humectant in that it acts as a film-former that attracts water and locks it into the skin. We have found that this product provides fatty vesicles of glycoprotein which are not absorbed by the skin but remain on the skin surface to provide the treatment mentioned above. The FLB preferably comprises between 12.5 percent and 25 percent and more preferably 20 percent of the contact medium.

The contact medium conveniently further comprises panthenol. Panthenol is a known humectant due to the fact that it attracts water strongly after being absorbed into the epiphelium. It is a precursor of vitamin B-5 (pantothenic acid) which plays an important part in wound healing, producing rapid epithelization of damaged skin. The panthenol preferably comprises 2.5 percent to 3.75 percent, preferably 3.0 percent of the contact medium.

The pharmaceutically acceptable cream i.e. the list of inactives in the contact medium comprises the following items in the following ranges

| | |
|---|---|
| Emulsifying Wax nf | 7.0–9.0% |
| Light Mineral Oil | 8.0–12.0% |
| PPG-5-Ceteth-20 | 2.0–3.0% |
| Oleth-(4) | 1.0–1.8% |
| Propylene Glycol | 3.0–5.0% |

-continued

| | |
|---|---|
| Butylated Hydroxytolune | 0.025–0.5% |
| Malic Acid | 1.0–2.0% |
| Sodium Malinate | 1.0–2.0% |
| Methyl hydroxyvenzoate | 0.8–2.0% |
| Phenoxyethanol | 0.5–0.6% |
| Purified Water | to volume |

The tape is preferably a microporous tape, preferably a paper tape. A convenient microporous tape is that product which is sold by 3M under the trade mark "MICROPORE". It is a self-adhesive tape which adheres to the skin even when a contact medium has been applied to it. Because the tape is microporous, it is permeable to air as well as to the contact medium. This provides a significant advantage over a fully occlusive material which promotes bacterial proliferation.

The contact medium is applied sparingly (conveniently less than 1 mL over 12 cm$^2$) to the exposed non-adhesive surface of the tape to cover the entire scar. The patient may bathe or shower with the tape exposed. After such bath or shower a small amount of contact medium is applied to the exposed surface of the tape and is rubbed in over the tape so as to penetrate the microporous tape and to come into contact with the skin about the scar tissue. But in any event the contact medium is applied sparingly to the exposed surface of the tape at least every night but preferably every morning and night. The contact medium impregnated tape will normally separate spontaneously from the skin after about seven to ten days. The tape and contact medium is immediately applied again. The process is continued until scar maturation takes place which we have found may be as little as three months as is evidenced by a mature white scar (in white skinned persons) or a mature flat scar (in persons of pigmented skin).

The most critical time period, however for scar management is the first two to six weeks, and we have found that where taping and contact medium is provided for this period, the taping alone may suffice thereafter until scar maturation.

This treatment conveniently commences after the removal of the sutures, which normally occurs after about one to three weeks after the operation.

We have found that patients react favourably to the limited steps they must take and consequently follow the required regimen to a very close degree. This ensures that the benefits of the procedure are obtained.

According to another aspect of the invention there is provided a medicament in the form of a contact medium or ointment for use in the treatment of scars, the medicament comprising a asiaticoside or operational portion thereof and (b) the *frutescens* from the leaf sap of the Bulbine species (FLB) in an aqueous carrier. Although the asiaticoside itself or the glycosides of the asiaticoside may be used, preferably the triterpenic fraction (or aglycone) of the asiaticoside should be used. If the glycosides are used then ten times the concentration would normally be required.

The asiaticoside which occurs naturally in *Asiatica centella* has the following structure:

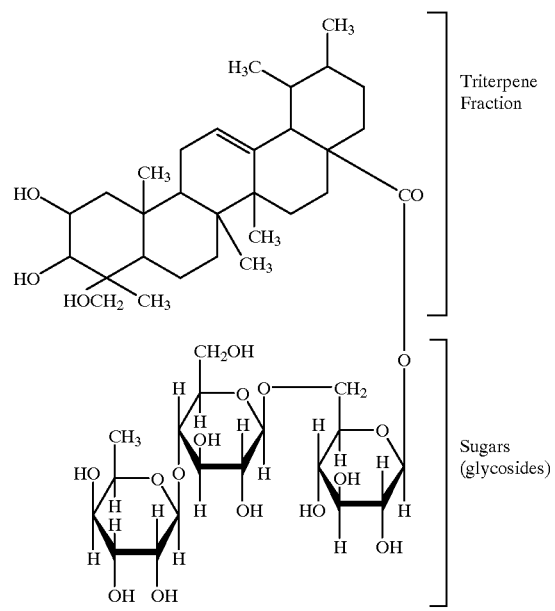

A typical medicament comprises TTF 1, panthenol 3%, FLB 20% in a pharmaceutically acceptable cream to 100%. Alternatively it may comprise glycoside 10%, panthenol 3%, FLB 20% in a pharmaceutically acceptable cream to 100%

According to a further aspect of the invention there is provided a medicinal kit comprising a medicament or contact medium incorporating constituents having properties capable of hydrating a scar, and preferably being as set out above, in combination with a microporous tape, the parts being arranged so that the tape can be applied to the skin and thereafter the medicament applied sparingly to the exposed face of the tape so that it may pass therethrough to the scar tissue below the tape.

We have found that the elements of the combination of the support, the hydration and active ingredients providing enhanced wound healing have a synergistic effect upon each other such that the wound heals and reaches maturity faster. This is because the various conditions that overstimulate the inflammatory process (e.g. movement and tension), are controlled by this combination. The substantially improved scar treatment can be appreciated because the objective appearance cosmetically of the scar is better and the sensitivity of the scar is also better. While important generally, the improved scar maturity and healing is particularly important in plastic surgery.

It will be appreciated that it is easy for the patient to apply the contact medium to the microporous tape each day and to replace the tape as and when necessary. Thus it is probable that the patient will comply with the doctor's instructions for the application of the contact medium. This will ensure that the scar is subject to the correct treatment with consequent beneficial results.

An example of the invention will now be described by way of illustration.

Nearly three hundred patients who had been subject to plastic surgery resulting in a post-operative scar were each treated as set out below:

The wounds were on various parts of the body's of the patients including the forehead, thigh, arm, breast, chest, sternum, abdomen and back of various patients. The post-operative wounds were of a range of lengths most from a few millimetres up to 20 to 30 centimetres.

As is usual, wounds were closed by sutures after surgery. Once the sutures are removed from the scar, 25 mm wide microporous tape (sold under the trade mark MICROPORE by the 3M company) is applied to the scar. The tape is applied running along the length of the scar and overlaps the sides of the scar by at least 10 mm.

The patient applies to the exposed surface of the tape a contact medium having the composition set out below. Thereafter the patient applies the contact medium to the exposed surface of the tape twice a day, morning and evening. The medium is applied very sparingly, less than 1 ml over 12 cm$^2$ area of tape and is rubbed on to the surface of the tape until a white sheen is evident—it is not rubbed in completely. After two to three minutes the cream is seen to be completely absorbed into the tape manifested by the dry surface of the tape which then acts as a slow release of active ingredient through the day until the next application. The patient showers or bathes with the tape in place. The tape remains in place until spontaneous separation takes place, usually at seven to ten days whereafter it is immediately replaced and the process is recommenced. The process continues until maturation of the scar takes places as manifested by the white flat appearing scar (in white skinned persons) or a mature flat scar (in persons of pigmented skin).

The contact medium comprises the following:

| | |
|---|---|
| TTF | 1.0% |
| emulsifying wax | 8.0% |
| FLB | 20.0% |
| light mineral oil | 10.0 |
| PPG-5-centeth-20 | 2.5 |
| Oleth (4) | 1.5 |
| Butylatedhydroxytoluene | 0.4 |
| Malic acid | 1.75 |
| Sodium Malinate | 1.75 |
| panthenol | 3.0 |
| propylene glycol | 4.0 |
| methyl hydroxybenzoate | 1.5 and |
| purified water | to volume |

We have found that almost all patients encountered no allergies, hypersensitivities or side effects related to the contact medium or tape. Two of the patients encountered temporary sensitivity to the tape but after a few days were able to resume the regimen. Patient compliance was excellent with no patients abandoning treatment which undoubtedly relates to the ease of use of the product. Excellent end results were seen in over 90% of patients. The scars were unobtrusive visually and aesthetically acceptable. The programme hastened occurrence of scar maturity which averaged three months as opposed to the four to six month period normally encountered without this treatment.

The patients were provided with a kit comprising the materials mentioned above which facilitated their use as all the materials were together and close at hand when required. Another advantage is that neither the tape nor the contact medium need be kept in a sterile container which facilitates the "home use" by the patient.

The invention is not limited to the preceding details. For example the microporous tape may be somewhat wider, say 50 mm. The tape may be impregnated with the contact medium. If necessary the patient may apply further contact medium only once daily.

If desired the contact medium may incorporate a constituent giving it an adhesive property. This contact medium would be applied to the scar before the tape is applied thereover.

The contact medium may be incorporated in a tissue glue substance which is applied to the incision. Thereafter a microporous tape will be applied to the scar and the contact medium is applied to the exposed surface of the tape to migrate on to the scar.

The contact medium may also be impregnated into the suture material, in particular to the dissolving suture material, for immediate treatment of the scar. The further treatment of the scar will be as described above.

The method above described may also be used for the treatment of scars other than post-operative scars resulting from wounds which are closed by sutures, these wounds may be of any length but to most will be a few millimetres to for example 20 to 30 centimetres.

The following references are cited herein:

1. Alster T S and West T B: Treatment of scars: A Review. Ann Plast Surg 39: 418, 1997

2. Clark R A F: Biology of Dermal Wound Repair. Dermatol Clinics 11: 647, 1993

3. Morris D E et al: Acute and Chronic Animal Models for Excessive Dermal Scarring: Quantitative Studies. Plast Reconstr Surg 100: 674, 1997

4. Sommerlad B C and Creasey J M: The Stretched Scar: A Clinical and Histological Study. Br J Plast Surg 31: 34, 1978.

5. Elliot D, Cory-Pearce R, Rees G M: The Behaviour of Presternal Scars in a Fair-skinned Population Ann R Coll Surg Engl 67: 238, 1985.

6. Langer K: "On the Anatomy and Physiology of the Skin" (1861) Translated by T. Gibson. Br J Plast Surg 31: 93, 1978

7. Meyer M and McGrouther D A: A Study Relating Wound Tension to Scar Morphology in the Presternal Scar Using Langers Technique. Br J Plast Surg 44: 291, 1991.

8. Hogstrom H, Haglund U, Zederfeldt B: Tension Leads to Increased Neutrophil Accumulation and Decreased Laparotomy Wound Strength. Surgery 107: 215, 1990

9. Martin C W and Muir I F K: The Role of Lymphocytes in Wound Healing. Br J Plast Surg 43: 655, 1990.

10. Reiffel R S: Prevention of Hypertrophic Scars by Long Term Paper Tape Application. Plast Reconstr Surg 96: 1715, 1995

11. Orentreich N, Berger R A, Auerbach R: Anhidrotic Effects of Adhesive Tapes and Occlusive Film. Arch Dermatol 94: 709, 1966.

12. Gordon B I, Maibach H I: Adhesive Tape Anhidrosis. Arch Dermatol 100: 429, 1969

13. Marples R R, Kligman A M: Growth of Bacteria under Adhesive Tapes. Arch Dermatol 99: 107, 1969

14. Reiter D: Methods and Materials for Wound Management: Otolaryng—Head and Neck surg 110: 550, 1994

15. Hofmann H, Maibach H I: Transepidermal Water Loss in Adhesive tape Induced Dermatitis. Contact Dermatitis 2: 171, 1976

16. Carpendale M T F, Sereda W: The Role of the Percutaneous Suture in Surgical Wound Infection. Surgery 58: 672, 1965

17. Edlich R F et al: Studies in the Management of the Contaminated Wound. J Surg Res 8:585, 1968

18. Chang C C, Kuo Y F, Chiu H C, Lee J L, Wong T W, Jee S H: Hydration, not Silicone modulates the effects of keratinocytes on fibroblasts. J Surg Res 59: 705, 19. Sawada Y, Sone K: Hydration and Occlusion Treatment for Hypertrophic Scars and Keloid. Br J Plast Surg 45: 599, 1992

20. Niessen F B, Letter: Effectiveness of Silicone Sheets in the Prevention of Hypertrophic Breast Scars. Ann Plast Surg 39: 547, 1997

21. Davey R B et al: Adhesive Contact Media—An Update on Graft Fixation and Burn Scar Management. Burns 17: 313, 1991

22. Hirshowitz B et al: Static Electric Field Induction by a Silicone Cushion for the Treatment of Hypertrophic and Keloid scars. Plast Reconstr Surg 101: 1173, 1998

23. Van den Helder C J M, Hage J J: Sense and Nonsense of Scar Creams and Gels. Aesth Plast Surg 18: 307, 1994.

24. Havlik R J: Vitamin E and Wound Healing. Plast Reconstr Surg 100: 1901, 1997

25. Bosse J P, Papillon J, Frenette G, Dansereau J, Cadotte M, Le Lorier J: Clinical Study of a New Antikeloid Agent. Ann Plast Surg 3: 13, 1979

26. El Hefnawi H: Treatment of Keloid with Asiaticoside. Dermatologica 125: 387, 1962

27. Rosen H. Blumenthal A, McCallum J: Effect of Asiaticoside on Wound Healing in the Rat. Proc Soc Exp Biol Med 52: 279, 1967

28. Lawrence J C: The Morphological and Pharmacological Effects of Asiaticoside upon Skin in vitro and in vivo. Eur J Pharmacol 1: 414, 1967

29. Lawrence J C: The Effect of Asiaticoside on Guinea Pig Skin. J Invest Dermatol 19:95,1967

30. Sasaki S, Shinkaih-Akashi Y, Kishihara Y: Studies on the Mechanism of action of Asiaticoside on experimental granulation tissue and cultured fibroblasts and its clinical application in systemic scleroderma. Acta Derm Venereal (Stockh) 42: 141,1972

31. Torre P H, Donnadieu J M, Braditch J L: Activite cicatisante de l'asiaticoside dans plais obstetricales du prinee. La Clinique 57: 203, 1963

32. Bonte F, Dumas M, Chaudagne C, Meybeck A: Influence of Asiatic Acid, Madecassic Acid and Asiaticoside on Human Collgen I Synthesis. Plata Med 60: 133, 1994

33. Bailey A J, Bazin S, Sims T J, Le Lous M, Nicoletis C, Delaunay A: Characterisation of the Collagen of Human Hypertrophic scars and Normal Scars: Biochim et Biophys Acta 405:412, 1975

34. Landes E: Konservative Therapie von Narben und Falten. Z Hautkr 62:805, 1987

35. Bonte F, Dumas M, Chaudagne C, Meybeck A: Asiaticoside and Madecassoside activity on human fibroblast type I and III collagen. Ann Pharmaceutiques Francaises 53: 38,1995

36. Tenni R: Effect of the triterpenoid fraction of *Centella asiatica* on macromolecules of the connective tissue matrix in human skin fibroblast cultures. Ital J Biochem 37: 69, 1988

37. Velasco M, Romero E: Drug interaction between asiaticoside and some anti inflammatory drugs in wound healing of the rat. Curr Ther Res 19: 121, 1976

38. Van Wyk B E, Van Oudthoorn B, Gericke N: Medicinal Plants of South Africa.Briza: South Africa 64, 1997

The publications mentioned in this specification are indicative to the levels of those skilled in the art to which the invention pertains. These publications are herein incorporated by reference to the same extent as if each individual publication was specifically and individually indicated to be incorporated by reference.

We claim:

1. A method of treating post-operative scars comprising (a) applying to the scar a tape which supports the scar in such a way as to minimise tension on the scar tissue and which permits the passage therethrough of a contact medium applied to the exposed surface of the tape so that medium will reach and treat the scar, and (b) then applying to the exposed surface of tape a contact medium incorporating a hydrating agent which is an expressed gel from the plane *Bulbine Frutescens*.

2. A method as claimed in claim 1 wherein the contact medium incorporates a constituent providing enhanced wound healing.

3. A method as claimed in claim 1 wherein the contact medium incorporates panthenol.

4. A method as claimed in claim 1 wherein the contact medium incorporates a triterpenic fraction of asiaticoside.

5. A method as claimed in claim 1 wherein the contact medium incorporates a glycoside portion of asiaticoside.

6. A method as claimed in claim 1 wherein the tape is a microporous tape.

7. A method as claimed in claim 6 wherein the tape is a paper tape.

* * * * *

UNITED STATES PATENT AND TRADEMARK OFFICE
CERTIFICATE OF CORRECTION

| | |
|---|---|
| PATENT NO. | : 6,159,494 |
| APPLICATION NO. | : 09/204982 |
| DATED | : December 12, 2000 |
| INVENTOR(S) | : Alan D. Widgerow and Laurence A. Chait |

It is certified that error appears in the above-identified patent and that said Letters Patent is hereby corrected as shown below:

At Column 8, line 30, please delete "plane" and insert --plant-- therefor.

Signed and Sealed this
Ninth Day of October, 2012

David J. Kappos
*Director of the United States Patent and Trademark Office*